United States Patent
Lauffer

(12) 
(10) Patent No.: US 6,523,010 B2
(45) Date of Patent: *Feb. 18, 2003

(54) ASSISTANCE METHOD AND APPARATUS

(75) Inventor: Randall B. Lauffer, Brookline, MA (US)

(73) Assignee: Keen.com, Inc., San Francisco, CA (US)

( * ) Notice: Subject to any disclaimer, the term of this patent is extended or adjusted under 35 U.S.C. 154(b) by 286 days.

This patent is subject to a terminal disclaimer.

(21) Appl. No.: 09/733,872

(22) Filed: Dec. 8, 2000

(65) Prior Publication Data

US 2001/0010043 A1 Jul. 26, 2001

Related U.S. Application Data

(63) Continuation of application No. 09/488,130, filed on Jan. 20, 2000, now Pat. No. 6,223,165
(60) Provisional application No. 60/125,557, filed on Mar. 22, 1999.

(51) Int. Cl.$^7$ ................................................ G06F 17/60
(52) U.S. Cl. ............................... 705/8; 705/1; 705/26; 379/265.05
(58) Field of Search ............................... 705/1, 3, 7, 8, 705/26; 379/265.05, 265.06, 265.12, 265.13

(56) References Cited

U.S. PATENT DOCUMENTS

| | | |
|---|---|---|
| 4,577,065 A | 3/1986 | Frey et al. |
| 4,631,428 A | 12/1986 | Grimes |
| 4,677,434 A | 6/1987 | Fascenda |
| 4,723,283 A | 2/1988 | Nagasawa et al. |
| 4,751,669 A | 6/1988 | Sturgis et al. |
| 4,847,890 A | 7/1989 | Solomon et al. |
| 5,058,152 A | 10/1991 | Solomon et al. |
| 5,148,474 A | 9/1992 | Haralambopoulos et al. |

(List continued on next page.)

FOREIGN PATENT DOCUMENTS

| | | |
|---|---|---|
| AU | 699785 | * 12/1995 |
| GB | 2 329 046 A | 10/1999 |
| GB | 2329046 A | 10/1999 |
| JP | 40923344 1 A | 9/1997 |
| JP | 40931981 2 A | 12/1997 |
| WO | WO 97/05733 | 2/1997 |
| WO | WO 98/02835 | 1/1998 |
| WO | WO 98/04061 | 1/1998 |
| WO | WO 98/13765 | 4/1998 |
| WO | WO 98/38558 | 9/1998 |

OTHER PUBLICATIONS

"USA Global Link Brings Interactively to Internet Shopping", Business Wire. Oct. 1998.

"Lucent Technology and Netscape Team to Deliver Lucent Ecommerce Solutions", Business Wire. Sep. 1998.

"TriNet's 'Help Me, I'm Stuck' Internet Voice Button Service Pushes Web Pages to Online Users", Business Wire. Mar. 1998.

(List continued on next page.)

Primary Examiner—Kyle J. Choi
Assistant Examiner—Susanna Meinecke-Diaz
(74) Attorney, Agent, or Firm—Blakely Sokoloff Taylor Zafman LLP

(57) ABSTRACT

This invention provides for a method of (or apparatus for) facilitating the delivery of advice to consumers using a server unit which can store and display the names and characteristics of experts and then rapidly assist in connecting the expert and consumer for real-time communication. The server can also have the ability to receive keywords from the consumer, match those keywords to one or more experts, and tell the consumer how to contact an expert.

47 Claims, 1 Drawing Sheet

Diverse Advice Sources

Information Flow:

Compensation for Advice:

U.S. PATENT DOCUMENTS

| | | |
|---|---|---|
| 5,319,542 A | 6/1994 | King, Jr. et al. |
| 5,325,424 A | 6/1994 | Grube |
| 5,347,632 A | 9/1994 | Filepp et al. |
| 5,359,508 A | 10/1994 | Rossides |
| 5,361,295 A | 11/1994 | Solomon et al. |
| 5,369,694 A | 11/1994 | Bales et al. |
| 5,497,502 A | 3/1996 | Castille |
| 5,537,314 A | 7/1996 | Kanter |
| 5,539,735 A | 7/1996 | Moskowitz |
| 5,555,298 A | 9/1996 | Jonsson |
| 5,557,677 A | 9/1996 | Prytz |
| 5,590,197 A | 12/1996 | Chen et al. |
| 5,602,905 A | 2/1997 | Mettke |
| 5,608,786 A | 3/1997 | Gordon |
| 5,619,148 A | 4/1997 | Sloane |
| 5,619,570 A | 4/1997 | Tsutsui |
| 5,619,725 A | 4/1997 | Gordon |
| 5,619,991 A | 4/1997 | Sloane |
| 5,634,012 A | 5/1997 | Stefik et al. |
| 5,638,432 A | 6/1997 | Wille et al. |
| 5,675,734 A | 10/1997 | Hair |
| 5,694,549 A | 12/1997 | Carlin et al. |
| 5,710,887 A | 1/1998 | Chelliah et al. |
| 5,712,979 A | 1/1998 | Graber et al. |
| 5,715,314 A | 2/1998 | Payne et al. |
| 5,717,860 A | 2/1998 | Graber et al. |
| 5,718,247 A | 2/1998 | Frankel |
| 5,721,763 A | 2/1998 | Joseph et al. |
| 5,722,418 A | 3/1998 | Bro |
| 5,724,424 A | 3/1998 | Gifford |
| 5,734,961 A | 3/1998 | Castille |
| 5,740,231 A | 4/1998 | Cohn et al. |
| 5,745,681 A | 4/1998 | Levine et al. |
| 5,768,348 A | 6/1998 | Solomon et al. |
| 5,768,521 A | 6/1998 | Dedrick |
| 5,778,367 A | 7/1998 | Wesinger, Jr. et al. |
| 5,794,221 A | 8/1998 | Egendorf |
| 5,809,119 A | 9/1998 | Tonomura et al. |
| 5,809,145 A | 9/1998 | Slik et al. |
| 5,812,769 A | 9/1998 | Graber et al. |
| 5,818,836 A * | 10/1998 | DuVal |
| 5,819,092 A | 10/1998 | Ferguson et al. |
| 5,819,267 A | 10/1998 | Uyama |
| 5,819,271 A | 10/1998 | Mahoney et al. |
| 5,819,285 A | 10/1998 | Damico et al. |
| 5,825,869 A | 10/1998 | Brooks et al. |
| 5,825,876 A | 10/1998 | Peterson, Jr. |
| 5,832,523 A | 11/1998 | Kanai et al. |
| 5,835,896 A | 11/1998 | Fisher et al. |
| 5,842,212 A | 11/1998 | Ballurio et al. |
| 5,850,433 A | 12/1998 | Rondeau |
| 5,860,068 A | 1/1999 | Cook |
| 5,862,223 A * | 1/1999 | Walker et al. |
| 5,864,871 A | 1/1999 | Kitain et al. |
| 5,870,744 A | 2/1999 | Sprague |
| 5,878,130 A | 3/1999 | Andrews et al. |
| 5,884,032 A | 3/1999 | Bateman et al. |
| 5,884,272 A * | 3/1999 | Walker et al. |
| 5,884,282 A | 3/1999 | Robinson |
| 5,890,138 A | 3/1999 | Godin et al. |
| 5,893,077 A | 4/1999 | Griffin |
| 5,907,077 A | 5/1999 | Glenn et al. |
| 5,907,677 A | 5/1999 | Glenn et al. |
| 5,911,132 A | 6/1999 | Sloane |
| 5,914,951 A | 6/1999 | Bentley et al. |
| 5,924,082 A | 7/1999 | Silverman et al. |
| 5,940,471 A | 8/1999 | Homayoun |
| 5,974,141 A | 10/1999 | Saito |
| 5,982,863 A | 11/1999 | Smiley et al. |
| 5,987,430 A | 11/1999 | Van Horne et al. |
| 5,991,394 A | 11/1999 | Dezonno et al. |
| 5,999,609 A | 12/1999 | Nishimura |
| 6,011,794 A | 1/2000 | Mordowitz et al. |
| 6,014,644 A | 1/2000 | Erickson |
| 6,026,087 A | 2/2000 | Mirashrafi et al. |
| 6,026,148 A | 2/2000 | Dworkin et al. |
| 6,026,400 A | 2/2000 | Suzuki |
| 6,029,141 A | 2/2000 | Bezos et al. |
| 6,035,021 A | 3/2000 | Katz |
| 6,046,762 A | 4/2000 | Sonesh et al. |
| 6,055,513 A | 4/2000 | Katz et al. |
| 6,058,379 A | 5/2000 | Odom et al. |
| 6,064,978 A | 5/2000 | Gardner et al. |
| 6,130,933 A | 10/2000 | Miloslavsky |
| 6,175,619 B1 | 1/2001 | DeSimone |
| 6,185,194 B1 | 2/2001 | Musk et al. |
| 6,188,673 B1 | 2/2001 | Bauer et al. |
| 6,192,050 B1 | 2/2001 | Stovall |
| 6,223,165 B1 | 4/2001 | Lauffer |
| 6,230,287 B1 * | 5/2001 | Pinard et al. ......... 379/265.09 |
| 6,259,774 B1 | 7/2001 | Miloslavsky et al. |

OTHER PUBLICATIONS

Tehrani, Rich, "E–Rip Van Winkle and the 60–Second Nap", Call Center Solution, vol. 18, No. 2, pp. 16(3). Aug. 1999.

"Netcall Internet Call–Buttons Enhance E–Commerce Customer Service and Sales", PR Newswire, p. 7431. Aug. 1999.

"Connecting to On–Line Car Shoppers: Auto Sellers Use NetCall Internet Call–Button Technology to Turn 'Clicks' Into Interactive Sales", PR Newswire, p. 4089. Jul. 1999.

Davey, Tom, "Wheeling and Dealing Online", PC Week, vol. 13, No. 45, pp. 1,129. Nov. 1996.

Collett, Stacy and Julia King, "Why Online Browsers Don't Become Buyers", ComputerWorld, vol. 33, No. 48, p. 14. Nov. 1999.

Information about Expertcity.com retrieved from the Internet URL: http://www.expertcity.com on Nov. 6, 2000. Nov. 2000.

"Rent–An–Expert On the Web", Information Week, p. 75. Sep. 1999.

"Expertcity.com Launches Premier Online Marketplace for Expert Services", PR Newswire. Aug. 1999.

Information about Keen.com retrieved from the Internet URL: http://www.keen.com on Oct. 24, 2000. Oct. 2000.

Peline, Jeff, "Net Firm to Connect Users By Phone", CNet News.com (retrieved from http://news.cnet.com on Oct. 24, 2000) Nov. 1999.

"Keen.com Launches First Live Answer Community", Press Release retrieved from http://www.keen.com on Oct. 24, 2000. Nov. 1999.

Healey, Jon, "From A to Z, You Can Sell Advice Online", Mercury News (retrieved from http://wwwO.Mercury-center.com on Oct. 24, 2000). Nov. 1999.

Menn, Joseph, "An Expert? There's Now a Home For You On The Internet", Los Angeles Times (retrieved from http://www.denverpost.com on Oct. 24, 2000) Nov. 1999.

"Walker Digital Issued Landmark U.S. application No. 5,862,223 for Global Internet Marketplace for Experts", Business Wire, Jan. 26, 1999.

Qcircuit Web Site (www.qcircuit.com).

Infomarkets.com Web Site (www.infomarkets.com).

Intellect Exchange Web Site (www.intellectexchange.com).

Answers.com Web Page (www.answers.com).

Ott, Chris, "Making Good On The Information Economy", Denver Business Journal, Dec. 17, 1999, p. 27A.

Rogers, Michael, et al., "Experts Abound At New Web Sites", Library Journal, Mar. 1, 2000, pp. 22–24.
"Surfbrains.com: Brains Online Save Time & Money", M2 Presswire, Jul. 11, 2000.
Hodgson, Cynthia, "Online Expert Databases & Services", Econtent, Dec. 1999, pp. 48–53.
Kanellos, Michael, "Do You Want To Know The Meaning of Life?", Computer Reseller News, Mar. 3, 1997, pp. 72–74.
"Applying Technology News", Accounting Technology, Feb./Mar. 1997, p. 14.
Greenblatt, Ellen, "Have You Ever Wondered . . . ", Datamation, Oct. 1997, p. 126.
Kabeya, Kiyoski, et al., "A New Teleconsultation Terminal System Using ISDN", NTT Review, Jul. 1991, vol. 3, No. 4, pp. 37–43.
Hase, Masahiko; Kawakubo, Shuji; Shoman, Mineo, "Advanced Videophone System Using Synchronized Video Filing Equipment", NTT Review, vol. 3, No. 4, Jul. 1991, pp. 29–36.
Mercalli, Franco; Negrini, Roberto, "The ESSAI Teleshopping System: An Example of a Broadband Multimedia Application", Publication No. 0–7803–1820–X/94, IEEE, 1994, pp. 572–576.
Asthana, Abhaya; Krzyzanowski, Paul, "A Small Domain Communications System For Personalized Shopping Assistance", Proceedings of ICPWC '94, Publication No. 0–7803–1996–6/94, IEEE, 1994, pp. 199–203.
Littleton, Linda, "Meet The Shadowy Future", Proceedings of ACM SIGUCCS User Services Conference XXII, Ypsilanti, Michigan, Oct. 16–19, 1994, pp. 205–_.
Ludwig, L.F.; Dunn, D.F., "Laboratory For Emulation And Study Of Integrated And Coordinated Media Communication", Conference on Office Information Systems, Mar. 23–25, 1988, Sponsored by ACM SIGOIS and IEEECS TC–OA in cooperation with IFIP W.G. 8.4, pp. 283–291.
Addeo, E.J.; Dayao, A.B.; Gelman, A.D.; Massa, V.F., "An Experimental Multi–Media Bridging System", Frontiers in Computer Communications Technology, Computer Communications Review, vol. 17, No. 5, Aug. 11–13, 1987, pp. 236–242.
ISDN Tutorial: Definitions, http://www.ralphb.net/ISDN/defs.html Apr. 21, 2000.
ISDN Tutorial: Interfaces, http://www.ralphb.net/ISDN/ifaces.html Apr. 21, 2000.

"The Voice of Technology", Credit World, pp. 20–23, Jul. 1994.
Telecommunications Buyers Guide and Directory, Editor & Publisher, pp. 29TC–38TC, Feb. 1994.
"Aspect Telecom: Aspect Integrates The Web Into The Call Center", M2 Presswire, Aug. 1996.
"Information, Bid and Asked", Forbes, Aug. 20, 1990, p. 92.
"Attachmate Ready to Answer 'Net Questions", Network World, Apr. 8, 1996, p. 37.
"US Courts To Launch First Federal 900 Service", Federal Computer Week, Sep. 28, 1992, p. 8.
"Company Devoted to Hot–Line Support", Computer Reseller News, Oct. 21, 1991, p. 48.
"For Telesphere's Clients, Dial '1–900 TUF Luck'", Business Week, Sep. 9, 1991, p. 88.
"When Business Plan And Real World Clash", Wall Street Journal, Jun. 9, 1999, p. B1.
"Hidden Cost of Tech Support", PC World, May 1995, p. 143.
"NetBazaar: Networked Electronic Markets For Trading Computation And Information Services", ECDL 1988— Research and Advanced Technology for Digital Libraries, p. 839.
"Multimedia Collaborative Remote Consultation Tools Via Gigabit WAN In Teleradiology", IEEE 1994, Phoenix, p. 417.
"Multimedia Communication In A Medical Environment", IEEE 1991 Singapore I.C. on Networks, p. 166.
"A New Teleconsultation Terminal System Using ISDN", NTT Review, Jul. 1991, p. 37.
"MiniPay: Charging Per Click On The Web", CNISDN, 1997, vol. 29, p. 939.
"Caring For Customers: Real–Time Text Chat And Telephony Provide Personalized Customer Support And Turn Queries Into Sales Leads", Internet World Media, Sep. 1999.
"Information for sale: Commercial Digital Reference and AskA Services", Virtual Reference Desk, Sep. 20, 1999, at www.vrd.org/AskA/commAskA.html.
Exp.com Web Site at www.exp.com/.
The Web Site at www.experts–exchange.com/.
Electronic Emissary at www.tapr.org/emissary/.
The Web Site at www.allexperts.com/.

* cited by examiner

Figure 1.a  Centralized Advice Sources
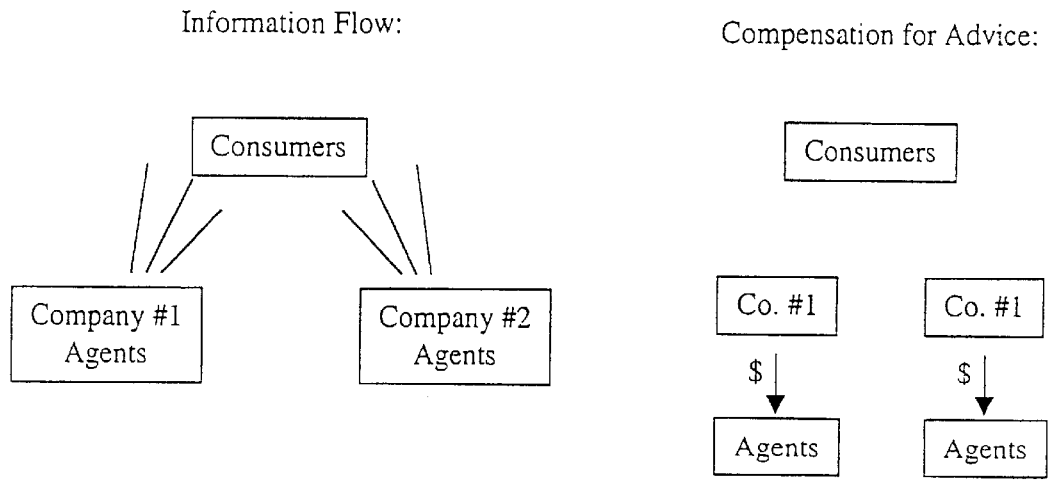
Figure 1.b  Diverse Advice Sources
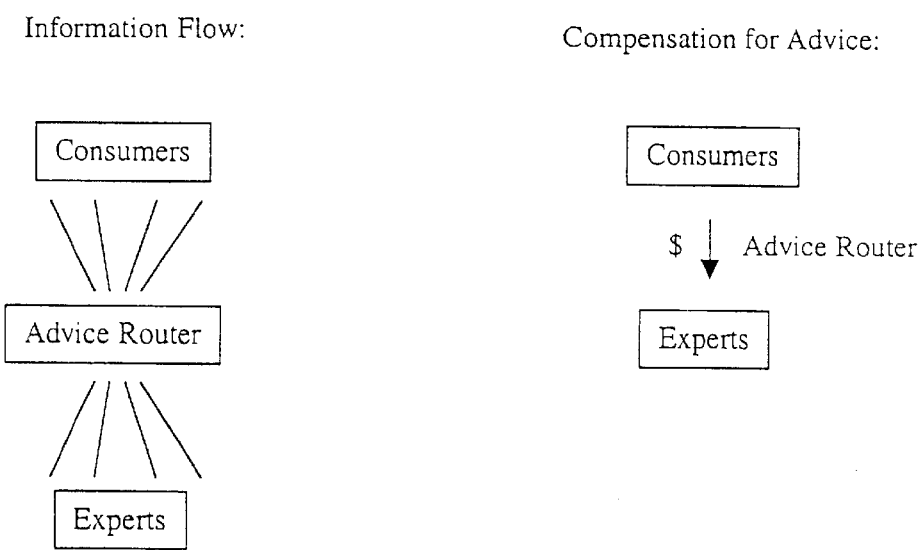

ASSISTANCE METHOD AND APPARATUS

This application is a continuation of application Ser. No. 09/488,130, filed on Jan. 20, 2000, now U.S. Pat. No. 6,223,165 B1, which claims benefit of provisional application No. 60/125,557, filed Mar. 22, 1999.

FIELD OF THE INVENTION

The present invention relates to techniques for delivering information electronically, more particularly, for delivering advice to consumers from a diverse set of experts. Still more particularly, the present invention relates to systems and methods for matching consumers questions with experts, displaying available experts for consumer viewing and selection, providing for compensation from consumers to experts, and providing for the connection between consumer and experts.

Definitions

Advice: Any needs of the consumer which can be provided for by an expert, including but not limited to conversation, entertainment, sounds or pictures of any kind, text, video, audio. This advice is not limited to that provided by agents regarding company products; it can include medical, legal, educational, travel, entertainment, religious, and other forms of advice. In addition, herein "advice" is meant broadly to include any type of information, comfort, or communication a consumer desires.

Consumers: Individuals, companies, organizations, governments, or devices which have one or more questions or needs for advice.

Experts: Individuals, companies, organizations, governments, or devices which are able to provide advice to consumers, provided that experts' initial means to contact consumers is via the server in the Advice Router. Experts' compensation, which may be zero, can come from either consumers directly or from the Advice Router. Collectively, experts represent a broader range of knowledge and experience than do agents which work for a single company. Much as the word "advice" is used broadly, "expert" is meant broadly since many types of information can be given by human beings.

Agents: Individuals, companies, organizations, governments, or devices who, as part of their relationship/employment at that institution, answers questions when connected to his institution's telephone or server, provided that the agent is paid by the institution for that function. The advice provided for by agents is generally restricted to that regarding products offered by their respective company.

Server: any device, network or software which connects consumers and experts.

Query: an action initiated by a consumer which includes keywords or other means to summarize their question or need for advice.

Expert characteristics: used for matching with consumers queries. Including, but not limited to one or more of the following: a code name which does not include his real name; keywords of expertise; number of years experience in each area of expertise; degrees earned; number of years of school after completion of high school or college; companies worked for or schools/training programs attended in the past or present; age; language; neighborhood, city, state, and/or country of residence; quality score as judged by previous consumer interactions; compensation rate for consumer advice; and whether the expert is available at the actual moment of consumers query or within 1,2,5,10, 15, 30, 60 minutes.

Matching: a process for scoring and putting in an order of relevance a list or selected list of experts who are likely to be able to answer a consumer's query. Can involve any method of assignment of numbers to the number of keyword matches or matches between ranges of characteristics desired by the consumer with the actual expert characteristics.

Logged in, or on-line: detectable means of communication between server and expert, including but not limited to telephone, Internet telephony, email, audio, and/or video.

Means to contact: any method, information, or technology used to bring together the consumer with one or more experts, including but not limited to telephone, Internet telephony, email, audio, and/or video. Means to contact includes telephone numbers (including toll-free and pay-per-call numbers), email addresses, Internet web pages or sites, video-conferencing details. More preferably, the means of contact includes telephone, Internet telephony, audio, and/or video, and even more preferably Internet telephony, audio and/or video, and even more preferably video. The technology to be used for any of the above includes TVs, TVs with set-top web browsers, PCs, telephones, and satellite connections.

Time-to-connect: the period of time between the transmission of the means of contact and the actual connection between expert and consumer. In the case where the consumer selects an expert, the time-to-connect is the period of time beginning when at the consumer's last action (e.g., clicking on the symbol for an expert or his telephone number) and ending when the actual connection is made. In the case where the server makes both connections, the time-to-connect is the period of time beginning when the server indicates to the consumer that it is beginning to contact the expert and ending when the actual connection is made.

BRIEF DESCRIPTION OF THE FIGURE

FIG. 1.$a$ shows the most common arrangement today of the advice business, known as Centralized Advice Sources, where there are a large number of consumers and few agents to help them at each company; this has the general shape of a funnel with too many questions going to too few agents.

FIG. 1.$b$ shows a fundamentally new advice technology structure, Diverse Advice Sources, wherein the actual companies selling products are not involved or only peripherally involved. Diverse Advice Sources more evenly equalizes the number of questions in the world at a given point in time with the number of experts who are likely to be able to answer their questions. This technology is in an hourglass shape where a large number of experts is available rather than the small number of agents at each company. In the middle is a new form of information company, the Advice Router, which rapidly facilitates the matching of and connection between consumers and experts.

BACKGROUND: PROBLEMS WITH CUSTOMER SERVICE AND GENERAL ADVICE

As more technology (videorecorders, personal computers, Internet, TV web boxes, cell phones, etc.) enters peoples' lives, there is greater and greater demand for help in choosing devices and solutions and in setting them up and correcting problems. Even more, generally, there is greater need for assistance in daily life, whether it is for medical, legal, family, or entertainment reasons.

At the same time that more information is required to conduct our lives, available effective sources of that information have not grown sufficiency in number or efficiency.

Companies selling products often have web pages or telephone support lines, but these are either too restricted in information, or the consumer must wait for long periods for live help.

To help with the routing of calls to available agents in a company, Cave (WO9813765) has devised a real-time system wherein a queuing manager routes calls to an agent who is free at the time. The system still involves automated answering systems which many consumers find frustrating, and it requires the hiring of not only agents but the queuing manager.

In the future, streaming audio and video capabilities on the web will make it possible for company agents to speak directly to consumers. However, this will be very costly to operate and the consumer will probably have to wait for long times to speak to one of the agents.

For general advice, the Internet is far too inefficient for many uses. Search engines return many hits, requiring the consumer to try many web sites and hope that the answer is available.

1-900 phone numbers (pay-per-call) are limited in scope and consumers hesitate to use them due to high per-minute rates, lack of trust in the billing, and generally perceived notions that the 900 numbers are for less-than-serious concerns such as astrology or sex chat. In addition, 900 services are small and narrowly focused, without the benefits of the Diverse Advice Sources arrangement, and they did not include matching and/or display technologies.

As shown in FIG. 1.a, the fundamental problem with current advice technologies is that there are a large number of consumers and few agents to help them at each company; this is known as Centralized Advice Sources, and the has the general shape of a funnel with too many questions going to too few agents. This leads to high cost (to pay agents and purchase systems), slow response time (long hold times on telephone), and lack of personal service (live agents). In addition, the agents often can only answer a limited range of questions regarding the companies products. Thus, the participation and control of the consumer advice function by each company is fundamentally hurting the company by frustrating consumers and by requiring it to staff, manage, and pay for a vast and complex undertaking which is outside of its main expertise (making widgets, providing a narrow service, etc.).

Previous solutions have not adequately filled the need, particularly for immediate advice or connection between appropriate people.

The American Information Exchange (AMIX) was a central exchange that attempted to mediate between buyers and sellers of information. But the complexity and lack of immediacy, among other problems, limited its ability to efficiently solve the buyer's problem.

Walker (U.S. Pat. No. 5,862,223) envisioned a similarly complex exchange, often involving several lengthy steps where a user request is submitted; a search of experts, even beyond its members, is undertaken; a portion of the user request (question) is transmitted to the computer-selected expert, etc. until the request if fulfilled. Walker (col 8, line 49; col 24, line 67) allows the user himself to select the expert from a general list, but there is no provision for seeing which expert is available at that instant to talk, and there is no provision to make the process of connecting the expert and user quickly, say within 1 min or 10 seconds. In addition the user must submit a portion of his question (end user request).

In the complex process described by Walker, the expert and user can communicate in real-time (col 9, line 1; col 26, line 49), but only after the process of submitting the end user request to the expert.

In another embodiment of Walker (col 28, line 66), the end user calls the central controller and eventually is put in touch with an expert for a real-time connection. No allowance is made for the central controller to make two separate calls (thus connecting the expert and user) after the user selects the expert.

In addition, there are no constraints in Walker on how fast the time-to-connect process needs to be to be useful. Timely information is more highly valued than delayed information.

Moreover, the detailed lists of experts and their characteristics (resumes, etc.) that are displayed in Walker (col 25, line 35) are not suitable for a system that fills the need for rapid selection and connection between parties; as the number of experts grows, there will be simply too many pages of text to scroll through. There is needed a new display system where users can rapidly survey the available experts via information rich graphics.

Walker does not take into account the use of experts as a workforce for customer support. No mention is made of product or service companies issuing certification for experts, and, in turn, those certifications listed or displayed explicitly by the central controller/server.

Description

In one embodiment, this invention provides for a fundamentally new advice technology structure, Diverse Advice Sources, wherein the actual companies selling products are not involved or only peripherally involved. Diverse Advice Sources more evenly equalizes the number of questions in the world at a given point in time with the number of experts who are likely to be able to answer their questions. As shown in FIG. 1.b this technology is in an hourglass shape where a large number of experts is available rather than the small number of agents at each company. In the middle is a new form of information company, the Advice Router, which rapidly facilitates the matching of and connection between consumers and experts.

The sheer number of experts available in Diverse Advice Sources solves the arithmetic (funnel) problem of Centralized Advice Sources, leading to the two most important benefits: fast response and the routine availability of live experts. In addition the diversity of sources raises the likelihood that the consumer will get more holistic advice, not limited to the tools available from any one company.

In another embodiment, this invention provides for a method of (or apparatus for) facilitating the delivery of advice to consumers, comprising:
  providing a server unit with the ability to store the names or identification of two or more experts, said experts coded by one or more expert characteristics, said server having the ability to detect which experts are online;
  said server having the ability to display at least one of said expert characteristics with information-rich graphics or symbols;
  said server having the ability to respond to a consumer's selection of expert by either sending the consumer a means to contact expert or by connecting the consumer and expert for real-time communication;
  wherein the time-to-connect between consumer and expert is 30 minutes or less.

In another embodiment, this invention provides for a method of (or apparatus for) facilitating the delivery of advice to consumers, comprising:
  providing a server unit with the ability to store the names or identification of two or more experts, said experts coded by one or more expert characteristics, said server having the ability to detect which experts are online;

said server unit having the ability to receive one or more keywords from a consumer;

said server unit having the ability to match those keywords to one or more experts and send the consumer a means to contact;

wherein the time-to-connect between consumer and expert is 30 minutes or less.

Certification

In the transition from central to diverse advice sources, companies will find that it is economical to broaden its customer support workforce to non-employees. While these non-employees may not have as detailed or as frequent training, they can answer many of the questions consumers have. Thus a company can offer simple tests and, optionally, transmit the results of those tests to the server, which maintains an up-to-date status of each expert. Alternatively, the company can simply give the certification to the expert who transmits the results to the server.

Certification tests can take many forms, including but not limited to web-based questionnaires, phone, Internet, or face-to-face interviews, live video connections, etc. Optionally, a company can use authentication procedures (fingerprint, voiceprint, "cookies" the expert's computer, passwords, etc.) to ensure the expert's identity. Optionally, the test and results can be cryptographically transmitted between the company and expert; or between the company and server.

Certification can also come from organizations or schools or governments.

Matching

In another embodiment, this invention provides for a matching system or relevance scoring method which finds the best expert to answer a consumer's question. This can involve any method of assignment of numbers to the number of keyword matches or matches between ranges of characteristics desired by the consumer with the actual expert characteristics. This technology is well known for search engines like Yahoo! for finding matches between a consumer's keywords and web pages as well as eBay for finding matches for merchandise. However, a system and method does not currently exist that allows one to match a wide array of features, including, but not limited to, two or more of the following expert characteristics: a code name which does not include his real name; keywords of expertise; number of years experience in each area of expertise; degrees earned; number of years of school after completion of high school or college; companies worked for or schools/training programs attended in the past or present; age; language; neighborhood, city, state, and/or country of residence; quality score as judged by previous consumer interactions; compensation rate for consumer advice; and whether the expert is available at the actual moment of consumers query or within 1,2,5,10, 15, 30, 60 minutes.

It is preferred that the number of categories in the list of expert characteristics used for matching be at least four, such as code name, keywords, compensation rate, and time availability. More preferably, the number of categories should be at least six. Even more preferably, the number of categories should be at least eight. Most preferred, the number of categories should be at least ten.

In another embodiment, this invention provides for a system for and method of displaying selected experts to the consumer. This includes, at a minimum, conveying, through means that include but are not limited to telephone, Internet telephony, email, audio, and/or video, a way for the consumer to contact the expert (the means of contact). It is more preferred for that conveyance to be performed by Internet telephony, email, audio, and/or video. It is most preferred for that conveyance to be performed by audio, and/or video.

The number of experts presented to the consumer can be at least one. It is more preferred that the number of experts presented to the consumer is at least two. It is even more preferred that the number of experts presented to the consumer is at least five. It is even more preferred that the number of experts presented to the consumer is at least ten. It is even more preferred that the number of experts presented to the consumer is at least 20. It is most preferred that the number of experts presented to the consumer is over 100.

In another embodiment, this invention provides for a system for and method of protecting the privacy and identity of both the expert and the consumer. If the expert prefers, his actual name, address and other information will be withheld from the consumer. Also, individual entries in the expert characteristics list can be shielded from view by the consumer. The consumer likewise can be protected. While privacy has been provided for in commercial/advertising technologies (see Goldhaber, U.S. Pat. No. 5,855,008), the shielding but still utilizing detailed expert characteristic lists has not been provided for.

Display

In addition to the mere conveyance of the means of contact, it is more preferred for the consumer to be presented with a visual display of available experts. Systems and methods have been used by Yahoo! and others for displaying game-playing individuals, with information related to availability for a game now, skill level, and code name. No such system or method exists for displaying expert characteristics.

Display methods include but are not limited to information-rich graphics such as objects with varying color or density, bar graphs, line graphs, 3-D graphs, icons, pictures, photographs, video. All of the above can include animation or motion to attract attention. Words and numbers can be added on or near any of the above to give further expert characteristics. Any of the above can be addressable by mouse/cursor location so that the consumer can easily select which expert to choose or which set of experts to zoom in on and view more closely. Optionally, zoom (magnification) and/or rotation functions can also be used. The zoom function can allow new and more detailed expert characteristics to appear with each increase in magnification. Similarly rotations of objects can reveal more detailed expert characteristics.

Useful expert characteristics that can be displayed visually include, but are not limited to: the expert's quality (rating) score, whether the expert is online now, or how long until he will be; whether the expert has a separate phone line, and whether it is busy or not.

A legend can optionally be provided when abstract symbols or colors are used so that consumers can tell what each symbol or color means.

In another embodiment, experts can select their own symbol, pictures, logos, etc. to advertise themselves. These include all of the above options. Optionally, they can use online avatars to represent themselves, with the additional option of the voice and facial expression of the expert transmitted to the consumer via this avatar.

In another embodiment, a special symbol/notation is displayed next to or as part of an experts symbol if he has been certified by selected companies or organizations. The symbol/notation can optionally expire, disappear, or change its characteristics (color, etc.) after a certain length of time so that the expert is forced to take tests to maintain certification.

In another embodiment, the display is a map either of geography, system or building architecture or any type of display where experts are, at that time, located or qualified in. The map and expert symbols on it is continually updated to see who is online and/or their exact or general location. The size of the symbol used for each expert is adjusted as the number of experts online increases so each can be displayed. Optionally the zoom function allows better viewing of crowded regions of the map.

This display method can be useful in cases where a consumer only wants information from someone at a particular location, e.g., to determine weather, sport conditions (ski, surf, etc), traffic, delivery/pickup truck availability, nature (animal sightings), entertainment (club-hopping), state or city laws, or any kind of location-dependent information.

Other types of non-geographical maps or diagrams can also be used, including but not limited to software architecture, flow charts, graphs, etc. Here the location of the expert's symbol is determined by their expertise in a particular subject within that map.

In some cases, if the expert is qualified in more than one area, two or more of his symbols may appear in a given map or diagram.

Graphicel displays (line or scatter plots, etc) can be used by the consumer to weigh different features of the experts before making a selection. The consumer can be given a choice of 2- or 3-dimensional, and what the axis of the graph represent: quality score, compensation rate, distance from the consumer, etc. The symbols for the available experts in a particular subject area are placed in their appropriate position of the graph and the consumer can see, for example a scattergram and pick a well-rated expert who is not too expensive.

It is more preferred that the display method graphically show at least the following two items: relevance score or order of preference of experts on the one hand, and the time availability of the expert on the other. The latter refers to whether the expert is available at the actual moment of consumers query or within 1, 2, 5, 10, 15, 30, 60 minutes. It is even more preferred that the display method graphically show at least the following three items: relevance score or order of preference of expert, the time availability of the expert, and the compensation rate for consumer advice with that expert. It is even more preferred that the display method graphically show at least the following four items: relevance score or order of preference of expert, the time availability of the expert, the compensation rate for consumer advice with that expert and the quality score as judged by previous consumer interactions. It is most preferred that the display method graphically show at least the following five items: relevance score or order of preference of expert, the time availability of the expert, the compensation rate for consumer advice with that expert, the quality score as judged by previous consumer interactions, and one item selected from the following list: number of years experience in each area of expertise; degrees earned; number of years of school after completion of high school or college; companies worked for or schools/training programs attended in the past or present; age; language; neighborhood, city, state, and/or country of residence.

Compensation

Diverse Advice Sources fundamentally changes the economics of the consumer advice business. As shown in FIG. 1, Diverse Advice Sources replaces the awkward arrangement in Centralized Advice Sources wherein individual companies are expected to pay for consumer advice (by paying their hired agents) when it is the consumer who is benefiting from the advice. Of course consumers had in the past expected companies to pay for this advice, to encourage the consumer to use their product and not products from competing companies. The companies respond by establishing limited consumer advice groups which are highly inefficient and costly to the company. In Diverse Advice Sources, the consumer pays for the advice information packet directly, to either or both of the expert and the Advice Router.

This invention also includes an alternative case where the consumer does not directly pay either the expert or the Advice Router. In this special case, general advertisements are used to fund the Advice Router, and the Advice Router either compensates the expert for his time, or the expert receives no direct compensation and instead gains some other value (e.g., advertising).

Unique payment systems and methods used by the Advice Router include but are not limited to the following:

a) credit card or (cyber-money) accounts for one or both of the consumer and expert; proper deductions and credits are made to each account after each transaction.

b) the means of contact can include a 900 number (or similar per-per-call/pay-per-view technology for the Internet); in this case, the consumer simply dials the 900 number given by and controlled or contracted for by the Advice Router, and the expert is paid according to well-known 900 number technology. This 900 number technology has been used in the past to provide advice from individual groups, but these activities did not include matching and/or display technologies, nor did they have the benefits of the Diverse Advice Sources arrangement.

c) other phone or media accounts.

Various payment schemes can be optimized to meet consumer and expert expectations. For example, rather that a flat per-hour, per-minute, or per-session rate, a number of schemes can be used to compensate for the consumer ensuring that the expert is adequate (for example, the first two minutes free), etc.

In all of these cases, the Advice Router can receive a fee for conveying the means of contact, and/or the connection.

Also, the Advice Router can pay or rebate a portion of the consumer charge if the consumer take some additional action, such as rating the quality of the expert, etc.

Connection

This invention provides for a system and method whereby the server used by the Advice Router can be used for providing for or aiding rapid connections and monitoring of interactions between consumers and experts.

Regarding the connection, it is preferred that the server provide for or facilitate a connection within 30 minutes after the means of contact has been conveyed to the consumer. It is more preferred that the time-to-connect is 10 minutes or less. It is even more preferred that the time-to-connect is 5 minutes or less. It is even more preferred that the time-to-connect is 2 minutes or less. It is even more preferred that the time-to-connect is 1 minute or less. It is even more preferred that the time-to-connect is 30 seconds or less. It is even more preferred that the time-to-connect is 20 seconds or less. It is most preferred that the time-to-connect is 10 seconds or less.

The connection can include any method or technology used to bring together the consumer with one or more experts, including but not limited to telephone, Internet telephony, email, audio, and/or video. More preferably, the connection-involves telephone, Internet telephony, audio, and/or video, and even more preferably Internet telephony, audio and/or video, and even more preferably video. The technology to be used for any of the above includes TVs, TVs with set-top web browsers, PCs, telephones, and satellite connections.

In the case where the consumer selects an expert on the Internet, the server can connect both using a two-step procedure wherein two separate and independent transmissions (e.g., telephone calls) are placed and then the two transmissions are joined together. This allows the server to store the expert addresses/phone numbers anonymously and control the connection.

The server should be able to monitor the interactions to provide for quality control and/or exact payment.

Example

Two experts, Joe and Bill, connect to the Advice Router and fill out forms describing their expertise. Joe is expert in Microsoft's Word and Powerpoint programs, and Bill is expert in the Word and Excel programs. The server detects that they are both logged on. Later that evening,.Bill is busy with a consumer for a period he estimates will be 15 more minutes. Joe is free. At that moment, David, a consumer, logs on and fills out a keyword query list that best suits his question: how to turn off the automatic spellchecker in Microsoft Word. He also gives his VISA credit card number via a secure link. A second after he finishes his entry, a display on his PC shows two color-coded boxes coinciding with the current list of available experts, Joe and Bill (only their code names are used, however). The relevance score for both is 1.0 (optimal) since both are experts in Microsoft Word. Both experts also charge the same rate, $1.00 per minute. However, a small box in Joe's area is clearly green and easy to read—this box corresponds to the fact that Joe is available at this instant to speak to David. (David does not select Bill since the red color in his box corresponds to a 15 min. wait or more.) David clicks an icon in Joe's, box and a second or two later, a streaming real-time video of Joe appears on David's PC, and if David's PC is so enabled, Joe sees David in his PC. They spend five minutes solving David's problem and log out. Prior to logging out, however, David receives a $0.50 rebate on the cost of the connection by rating the quality of Joe's help, from 0 for "awful" to 10 for "great". The cost of David's call is $5.00 minus $0.50 or $4.50; in his case, this is added to his monthly $50–$100 phone/Internet bill.

For maintaining the site, the Advice Router deducts $1.00 from the net $4.50 received and remits $3.50 to Joe. If David had not elected to receive the $0.50 rebate, the Advice Router would have made $1.50 on the call.

For most of its experts, the Advice Router takes out 30% before paying the experts.

Those skilled in the art will know that this example is illustrative only and does not in any way limit the range of applications of the present invention.

I claim:

1. A method of connecting two parties in real time, the method comprising:

displaying a list of experts to a consumer via an internet connection with said consumer prior to the consumer submitting a question;

the list indicating individually whether each expert is currently available to telephonically communicate with said consumer at a time when said consumer is viewing the list, said list includes a compensation rate for each expert;

in response to the consumer selecting a displayed icon corresponding to an expert from the list, automatically establishing a telephone connection between the expert and the consumer prior to the consumer submitting a question to the expert; and said automatically establishing the telephone connection includes a central controller placing a telephone call to said consumer, and said central controller placing a telephone call to said expert.

2. The method as described in claim 1, further comprising, after the real time communication connection has ended, prompting the consumer to provide a quality score for the expert.

3. The method as described in claim 1, wherein the indication of each expert's availability includes an information-rich graphic.

4. The method as described in claim 1, wherein the list includes an avatar representation for each expert.

5. The method as described in claim 1, wherein the list includes an indication of the expert's certification.

6. The method as described in claim 1, wherein the list includes a compensation rate for each expert.

7. The method as described in claim 6, wherein the compensation rate includes a rate per period of time.

8. The method as described in claim 1, wherein the list includes a quality score provided by previous consumers.

9. The method as described in claim 1, wherein the list is provided in response to a keyword search.

10. The method as described in claim 9, wherein the keyword search includes matching based upon a plurality of expert characteristics.

11. The method as described in claim 1, wherein the list is provided in response to a category selection.

12. The method as described in claim 1, wherein said telephone connection is an internet telephony connection.

13. The method as described in claim 1, wherein the real time communication connection includes a video connection.

14. The method as described in claim 1, wherein the real time communication connection is established without disclosing identity information about the expert to the consumer and without disclosing identity information about the consumer to the expert.

15. The method as described in claim 1, further comprising: monitoring how long the real time communication connection is maintained between the expert and the consumer.

16. The method as described in claim 15, further comprising, billing the consumer based upon how long the real time communication connection is maintained.

17. The method as described in claim 15, further comprising:

setting up an account for the expert; and crediting the account for an amount based upon how long the real time communication connection is maintained.

18. The method as described in claim 15, further comprising:

setting up an account for the expert; and crediting the account for an amount based upon how long the real time communication connection is maintained minus a fee.

19. The method as described in claim 1, further comprising: setting up a consumer account for the consumer.

20. The method as described in claim 19, wherein setting up the consumer account includes obtaining credit card information from the consumer.

21. The method as described in claim 19, further comprising:

monitoring how long the real time communication connection is maintained between the expert and the consumer; and deducting from the consumer account an amount based upon how long the real time communication connection is maintained.

22. A system for connecting two parties in real time, the system comprising:

a database to store information about a plurality of experts;

a first logic unit linked with the database to display a list of experts to a consumer via an internet connection with said consumer prior to the consumer submitting a question, the list indicating individually whether each expert is currently available to telephonically communicate with said consumer at a time when said consumer is viewing the list, said list includes a compensation rate for each expert; and a second logic unit linked with the database to automatically establish, in response to the consumer selecting a displayed icon corresponding to an expert from the list, a telephone connection between the consumer and the expert prior to the consumer submitting a question to the expert;

said second logic unit automatically establishing the telephone connection by a central controller placing a telephone call to said consumer, and said central controller placing a telephone call to said expert.

23. The system as described in claim 22, wherein the server has a third logic unit to prompt the consumer to provide a quality score for the expert after the real time communication connection has ended.

24. The system as described in claim 23, wherein the quality score is stored on the database.

25. The system as described in claim 22, wherein the first logic unit provides the list of experts in response to a keyword search.

26. The system as described in claim 22, wherein the first logic unit is capable of matching based upon a plurality of expert characteristics.

27. The system as described in claim 22, wherein the first logic unit provides the list of experts in response to a category selection.

28. The system as described in claim 22, wherein the telephone connection is an internet telephony connection.

29. The system as described in claim 22, wherein the real time communication connection includes a video connection.

30. The system as described in claim 22, wherein the real time communication connection is established without disclosing identity information about the expert to the consumer and without disclosing identity information about the consumer to the expert.

31. The system as described in claim 22, wherein the server has a third logic unit to monitor how long the real time communication connection is maintained between the consumer and the expert.

32. The system as described in claim 31, wherein the server has a fourth logic unit to bill the consumer based upon how long the real time communication connection is maintained.

33. The system as described in claim 31, wherein the database further stores information about an account set up for the expert, and the server has a fourth logic unit linked with the database to credit the account for an amount based upon how long the real time communication connection is maintained.

34. The system as described in claim 31, wherein the database further stores information about an account set up for the expert, and the server has a fourth logic unit linked with the database to credit the account for an amount based upon how long the real time communication connection is maintained minus a fee.

35. The system as described in claim 22, wherein the database stores information about a consumer account set up for the consumer.

36. The system as described in claim 35, wherein the information about the consumer account includes credit card information obtained from the consumer.

37. The system as described in claim 35, wherein the server has:

a third logic unit to monitor how long the real time communication connection is maintained between the consumer and the expert; and a fourth logic unit linked with the database to deduct from the consumer account an amount based upon how long the real time communication connection is maintained.

38. A computer-readable medium having stored thereon instructions which, when executed by a computer, cause the computer to perform a method comprising:

displaying a list of experts to a consumer via an internet connection with said consumer prior to the consumer submitting a question, the list indicating individually whether each expert is currently available to telephonically communicate with said consumer at a time when said consumer is viewing the list, said list includes a compensation rate for each expert;

in response to the consumer selecting a displayed icon corresponding to an expert from the list, automatically establishing a telephone connection between the expert and the consumer prior to the consumer submitting a question to the expert; and said automatically establishing the telephone connection includes a central controller placing a telephone call to said consumer, and said central controller placing a telephone call to said expert.

39. The computer-readable medium as described in claim 38, having stored thereon instructions that further cause the computer to prompt the consumer to provide a quality score for the expert after the expert has finished communicating with the consumer.

40. The computer-readable medium as described in claim 38, having stored thereon instructions that further cause the computer to monitor how long the real time communication connection is maintained between the expert and the consumer.

41. The computer-readable medium as described in claim 40, having stored thereon instructions that further cause the computer to bill the consumer based upon how long the real time communication connection is maintained.

42. The computer-readable medium as described in claim 40, having stored thereon instructions that further cause the computer to:

set up a consumer account for the consumer; and deduct from the consumer account an amount based upon how long the real time communication connection is maintained.

43. The computer-readable medium as described in claim 40, having stored thereon instructions that further cause the computer to:

set-up an account for the expert; and credit the account for an amount based upon how long the real time communication connection is maintained.

44. The computer-readable medium as described in claim 40, having stored thereon instructions that further cause the computer to:

set-up an account for the expert; and credit the account for an amount based upon how long the real time communication connection is maintained minus a fee.

45. The computer-readable medium as described in claim 38, wherein the telephone connection is an internet telephony connection.

46. The computer-readable medium as described in claim 38, wherein the instructions stored thereon cause the computer to establish a video connection in response to the consumer selecting the expert.

47. The computer-readable medium as described in claim 38, wherein the instructions stored on the computer-readable medium cause the computer to establish the real time communication connection without disclosing identity information about the expert to the consumer and without disclosing identity information about the consumer to the expert.

* * * * *